(12) United States Patent
Wu et al.

(10) Patent No.: US 8,247,004 B2
(45) Date of Patent: Aug. 21, 2012

(54) PLANT EXTRACTS FOR TREATING SKIN DISORDERS AND ENHANCING HEALING OF WOUNDS FOR DIABETIC PATIENTS

(75) Inventors: Rey-Yuh Wu, Xizhi (TW); Yuh-Shan Chung, Xizhi (TW); Yu-Yuan Wu, Xizhi (TW); Ma-Li Siu, Xizhi (TW); Hung-Jen Huang, Xizhi (TW); Chin-Wen Hsiao, Xizhi (TW)

(73) Assignee: Development Center for Biotechnology, Xizhi, Taipei County (TW)

( * ) Notice: Subject to any disclaimer, the term of this patent is extended or adjusted under 35 U.S.C. 154(b) by 0 days.

(21) Appl. No.: 13/161,054

(22) Filed: Jun. 15, 2011

(65) Prior Publication Data

US 2012/0009281 A1    Jan. 12, 2012

Related U.S. Application Data

(62) Division of application No. 11/605,178, filed on Nov. 28, 2006, now Pat. No. 7,985,431.

(30) Foreign Application Priority Data

Dec. 22, 2005 (TW) ................................ 94145941 A

(51) Int. Cl.
*A61K 36/53* (2006.01)
*A61P 17/02* (2006.01)
(52) U.S. Cl. ........................................ 424/725
(58) Field of Classification Search .................. None
See application file for complete search history.

(56) References Cited

U.S. PATENT DOCUMENTS

| 4,318,906 | A | 3/1982 | Llopart |
| 5,834,437 | A | 11/1998 | Jew et al. |
| 6,267,996 | B1 | 7/2001 | Bombardelli et al. |
| 6,417,349 | B1 | 7/2002 | Kim et al. |
| 6,475,536 | B2 | 11/2002 | Bombardelli et al. |
| 6,579,543 | B1 | 6/2003 | McClung |
| 7,531,194 | B2 * | 5/2009 | Wu et al. ............. 424/725 |
| 2006/0099283 | A1 | 5/2006 | Wei et al. |

FOREIGN PATENT DOCUMENTS

| JP | 09-078062 | * | 3/1997 |
| JP | 2004-59482 | * | 2/2004 |

OTHER PUBLICATIONS

Translation of Sakanaka et al. of JP 2004-59482 of Feb. 2004.*
Translation of Udagawa et al. of JP 09-078062 of Mar. 1997.*
Lukhoba et al. Journal of Ethanopharmacoology. 2006; 103 (1): 1-24.*

* cited by examiner

*Primary Examiner* — Shanon A Foley
(74) *Attorney, Agent, or Firm* — Ladas & Parry LLP

(57) ABSTRACT

The present invention provides a pharmaceutical composition for treating skin disorders, including enhancing the healing of wounds for diabetic patients. Specifically, this invention relates to the use of the extracts of *Plectranthus amboinicus* and *Centella asiatica* for improving skin disorders, including enhancing the healing of wounds for diabetic patients, and a pharmaceutical composition comprising the extracts of *Plectranthus amboinicus* and *Centella asiatica* as well as a wound dressing comprising the same. The invention also provides a method for preparing the crude extract and extract of *Plectranthus amboinicus*.

3 Claims, 9 Drawing Sheets

PLANT EXTRACTS FOR TREATING SKIN DISORDERS AND ENHANCING HEALING OF WOUNDS FOR DIABETIC PATIENTS

CROSS REFERENCE TO RELATED APPLICATIONS

This application is a divisional of application Ser. No. 11/605,178 filed on Nov. 28, 2006, which granted as U.S. Pat. No. 7,985,431, which claims the benefit of priority of Taiwanese Patent Application 094145941 filed on Dec. 22, 2005, which is incorporated herein by reference.

FIELD OF THE INVENTION

The present invention relates to Chinese herbal medicine extracts. Specifically, the present invention relates to the use of the extracts of *Plectranthus amboinicus* Benth and *Centella asiatica* Urban for treating skin disorders, including enhancing the healing of wounds for diabetic patients.

BACKGROUND OF THE INVENTION

*Plectranthus amboinicus* Benth (Patchouli), growing in Malaysia and India, is a decorative medicinal herb commonly cultivated by common families. The medicinal part of *Plectranthus amboinicus* Benth is the epigeal portion. *Plectranthus amboinicus* Benth is also known as Cuban oregano, Indian borage, Indian mint, Mexican mint, Mexican oregano or Spanish thyme. The Eastern Indians use *Plectranthus amboinicus* Benth as fabric aromatics, and the English discovered its attractive fragrance when importing shawl fabrics from India in the 1820's. When the *Plectranthus amboinicus* Benth leaves are put directly with clothing, it not only has an aromatic effect, but also prevents the clothing from being eaten by moths. It is thought to have uses for disinfection, excitement and preventing insect bites. In addition, *Plectranthus amboinicus* Benth may be used for treating poisonous snake bites, and relieving symptoms such as headache, flatulence, vomiting, diarrhea and fever. Moreover, *Plectranthus amboinicus* Benth oil is a popular perfume in Asia, and it is used for improving epithelia regeneration, treating acne, and relieving the symptoms of eczema, Athlete's foot and dry cracking skin in aromatherapy. Furthermore, *Plectranthus amboinicus* Benth is a good tranquilizer and aphrodisiac that can relieve anxiety and enhance sexual desire.

*Centella asiatica* Urban (pennywort) is a plant naturally growing in the coast area of Madagascar and the Indian Ocean. The medicinal part of *Centella asiatica* Urban of the Apiaceae family is its dried whole plant. *Centella asiatica* Urban is also known as European water-marvel, Gotu kola, Kola, Indian pennywort, Indian ginseng, Horse-hoof grass, Pegaga, Mandookaparni, Tiger herbal, Spadeleaf, or Tono. For hundreds of years, *Centella asiatica* Urban has been thought to be useful in the traditional medicines for improving wound healing in Asian regions. The extracts of *Centella asiatica* Urban comprise two major compounds: asiaticoside and madecassic acid. The uses of *Centella asiatica* Urban extracts are in treating burn wounds, trauma, and preventing postoperative adhesion, and the preparation methods of *Centella asiatica* Urban extracts have been described in some patent applications. For example, U.S. Pat. No. 4,318,906 and CN 1353972A disclose the medical uses of *Centella asiatica* Urban as the single active ingredient; U.S. Pat. No. 6,475,536, U.S. Pat. No. 6,267,996, CN 1313124A, CN 93110425.4 and CN 1089497A disclose the use of *Centella asiatica* Urban in combination with other substances for cosmetic formulation, treating burns or making ointment for trauma; and U.S. Pat. No. 5,834,437, U.S. Pat. No. 6,417,349 and CN 1194154A disclose the methods for preparing *Centella asiatica* Urban extracts.

The functions of skin include protection, excretion, secretion, absorption, heat regulation, storage, sensation and immune process regulation. When a wound occurs on the skin, for example, a wound caused by general trauma or a bedsore, it will cause an adverse effect on the skin and interfere with its normal functions. Diabetes mellitus is a common and chronic worldwide disease. According to the statistical report of the Department of Health, Executive Yuan, Taiwan, R.O.C. published in 2002, mortality due to diabetes increased from 7.9 deaths per 100,000 persons in 1980 to 39.3 deaths per 100,000 persons in 2002. The most common diabetes complications are neuropathy and angiopathy. Autonomic neuropathy causes reduction of sweating and results in dry cracking skin. Sensory neuropathy makes the patient insensitive to pain. Angiopathy causes macro- or micro-vascular obstructions, poor circulation, and atrophy of the skin. Once the wound is infected in a diabetic patient, it is difficult to be treated because not only controlling the bacterial infection but also the healing of the wound must be achieved. The only commercial therapeutic medicine available on the market for healing of wounds for diabetic patients is the gene recombinant product PDGF Regranex Gel (Becaplermin 0.01%) and it is very expensive. Therefore, it is necessary to provide new medicaments for enhancing the healing of wounds for diabetic.

SUMMARY OF THE INVENTION

One of the purposes of the present invention is to provide a pharmaceutical composition for treating skin disorders (including enhancing the healing of wounds for diabetic patients), comprising a therapeutically effective amount of *Plectranthus amboinicus* Benth crude extracts/extracts and a therapeutically effective amount of *Centella asiatica* Urban extracts.

Another purpose of the present invention is to provide a use of a combination of *Plectranthus amboinicus* Benth crude extracts/extracts and *Centella asiatica* Urban extracts for the manufacture of a medicament for treating skin disorders.

Another purpose of the present invention is to provide a wound dressing comprising the pharmaceutical composition of this invention.

Still another purpose of the present invention is to provide a method for preparing *Plectranthus amboinicus* Benth crude extracts/extracts.

A further purpose of the present invention is to provide a method for treating a skin disorder comprising administering a pharmacologically effective amount of a pharmaceutical composition of this invention.

The present invention is described in detail in the following sections. Other characterizations, purposes and advantages of the present invention can be easily found in the detailed descriptions and claims of the invention.

DETAILED DESCRIPTION OF THE INVENTION

Figure 1:
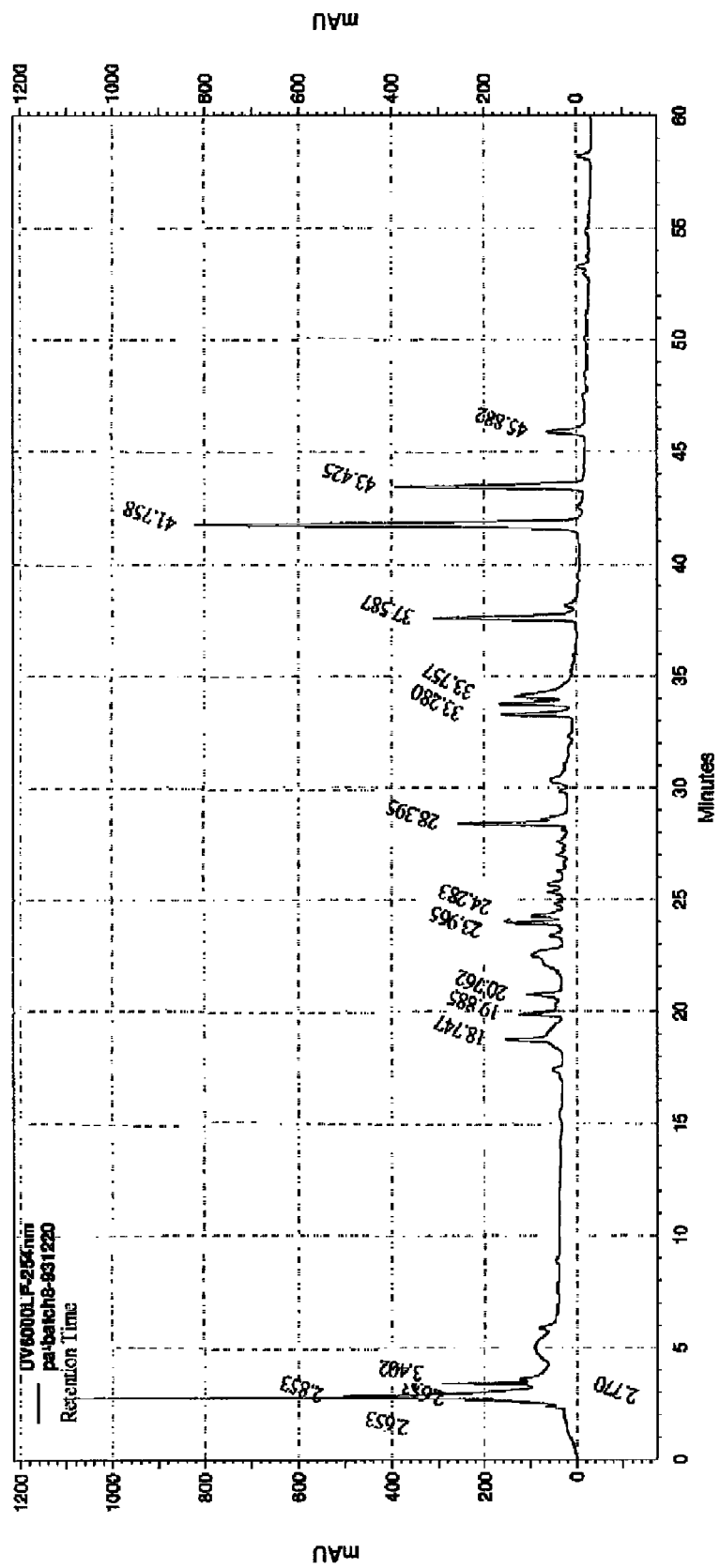
FIG. 1 shows the chromatography spectrum of extracts (PAet) extracted from alcohol-dipped, dried *Plectranthus amboinicus* Benth by Reverse Phase HPLC at UV 254 nm.

The term "skin disorders" as used herein includes wounds or sores. In one embodiment, skin disorders include a cut, laceration, abrasion, stab or other similar skin injuries, preferably a diabetic patient's wound; sores include bedsores.

The term "treating" or "enhancing" as used herein denotes improving the symptoms.

The term "patients" as used herein denotes animals, especially mammals. In one preferred embodiment, the term "patients" denotes "humans."

The term "therapeutically effective amount" as used herein refers to the amount of the pharmaceutical composition used alone or in combination with other medicaments for treating disorders that shows therapeutic efficacy.

The term "carrier" or "pharmaceutically acceptable carrier" refers to diluents, excipients, acceptors or analogues, which are well known to persons of ordinary skill in the art for manufacturing pharmaceutical compositions.

The term "*Centella asiatica* Urban extracts" denotes extracts of dried *Centella asiatica* Urban whole plants, wherein the major active components comprise asiaticoside and madecassic acid. Preferably, it is the medicinal part available on the market that mainly comprises asiaticoside and madecassic acid, and its purity is greater than 70%.

The term "*Plectranthus amboinicus* Benth crude extracts" or "*Plectranthus amboinicus* Benth extracts" denotes extracts obtained from extracting the epigeal portion of *Plectranthus amboinicus* Benth.

The present invention is characterized by using the combination of *Plectranthus amboinicus* Benth crude extracts/extracts and *Centella asiatica* Urban extracts for treating skin disorders including enhancing the healing of wounds for diabetic patients.

The present invention herein provides a pharmaceutical composition for treating skin disorder (including enhancing the healing of wounds for diabetic patients), comprising a therapeutically effective amount of *Plectranthus amboinicus* Benth crude extracts/extracts and a therapeutically effective amount of *Centella asiatica* Urban extracts. Said pharmaceutical composition can be used for treating disorders including but not limited to wounds and sores. In one preferred embodiment, said disorders are general trauma and bedsores, more preferably a diabetic patient's wound.

The pharmaceutical composition of the present invention can be applied topically to the wounds, and it may be formulated as a spray or non-spray. A spray form includes spray or solution; a non-spray form may be semi-solid or solid, preferably a solid form having a kinematic viscosity greater than water. Suitable formulations include but are not limited to suspensions, emulsions, creams, ointments, liniments and the like. If necessary, it may be sterilized or mixed with any pharmaceutically acceptable carriers, for example, stabilizers, wetting agents and the like. Preferably, the pharmaceutical composition of the invention is formulated as ointments, wherein the preferred pharmaceutically acceptable carriers include but are not limited to higher fatty acids, waxes, lipids, glycerol, higher alcohols or synthetic lipids. The pharmaceutical composition of the present invention, no matter which form it is formulated in, may further comprise emollients, fragrances or colors to increase the acceptability for various uses.

The pharmaceutical composition of the present invention may be conveniently used for manufacturing a wound dressing comprising a therapeutically effective amount of *Plectranthus amboinicus* Benth crude extracts/extracts and a therapeutically effective amount of *Centella asiatica* Urban extracts, wherein said wound dressing includes but is not limited to a bandage with adhesive, plaster patch and the like.

The pharmaceutical composition of the present invention may be prepared by persons of ordinary skill in the art using conventional methods. One embodiment of the present invention includes a method of preparing an ointment comprising the following steps:

heating the ointment base (BETAMETHASONE ointment base, Sinphar; Taiwan) in a water bath at about 50° C. until softened;

adding the softened ointment base in turn into the beaker containing frozen dried *Plectranthus amboinicus* Benth extracts;

adjusting the amount of ointment base and *Plectranthus amboinicus* Benth extract, the weight ratio being 99.75:0.25, to make the 0.25% *Plectranthus amboinicus* Benth extract ointment;

homogenously mixing 0.25% *Plectranthus amboinicus* Benth extract ointment and *Centella asiatica* Urban extracts in a weight ratio of 97:3 to make the 3% *Centella asiatica* Urban extract+0.25% *Plectranthus amboinicus* Benth extract ointment; and storing the ointment at 4° C. in a refrigerator.

The preparation method for the *Centella asiatica* Urban extracts, the active component in the pharmaceutical composition of the present invention, is well known to persons of ordinary skill in the art of herbal medicine extraction. The preferred method comprises:

extracting *Centella asiatica* by ethanol reflux extraction for 2 hours, and repeating it 2 to 3 times;

condensing the ethanol extract fluids to obtain the extracts;

retrieving the ethanol extracts, mixing and dissolving the extracts in water;

extracting with petroleum ether, chloroform, ethyl acetate separately, and then extracting with water-saturated n-butanol;

retrieving the solvent of n-butanol extracts under reduced pressure to obtain a cream-like substance and dissolving the substance in a small amount of methanol;

adding anhydrous acetone, several-fold, to the solution, to precipitate a yellowish crude total glucoside, drying and weighting the sediments;

a small amount of methanol is added to dissolve the crude total glucoside, mixing properly with silica gel and drying the mixture;

wet column packing with silica gel for chromatography and loading the sample silica gel;

eluting with chloroform, methanol and water (16:6:1 homogenous mixture) and collecting 18 components in turn; each component is 50 ml and the components are thin-layer spotting to compare with known controls;

combining components 9 to 15, concentrating, and then purifying with column using chloroform, methanol and water (14:6:1 homogenous mixture) for elution; and concentrating the same components and crystallizing with methanol repeatedly to obtain the white aciculate crystalline asiaticoside.

Furthermore, the drug substance containing asiaticoside and madecassic acid, with a purity greater than 70%, is available on the market.

The present invention also provides the preparation methods for *Plectranthus amboinicus* Benth crude extracts and extracts.

Preparation of *Plectranthus amboinicus* Benth Crude Extracts

Wash the fresh drug substances of *Plectranthus amboinicus* Benth with water, then extract the juice with a juice extractor. Freeze-dry the *Plectranthus amboinicus* Benth juice to obtain dry powders. Use a suitable solvent, for example, chloroform or methanol, to extract the *Plectranthus amboinicus* Benth crude extracts.

Preparation of *Plectranthus amboinicus* Benth Extracts

Dip a fixed amount of *Plectranthus amboinicus* Benth dry materials in a proper amount of high-polarity solvent. After filtration, dip again with a proper amount of high-polarity solvent and concentrate the *Plectranthus amboinicus* Benth extract solution with a reduced pressure rotary evaporator until its volume is 2-3% of the original volume. Dilute with solvent and separate by column. Optionally, it can be eluted continuously with four different solvents comprising high- to low-polarity solvents (namely high-polarity solvent, sub-high-polarity solvent, medium polarity solvent and low-polarity solvent). According to the present invention, high-polarity solvents include but are not limited to water, methanol, isopropanol, or a mixture of two or more of the preceding solvents. Low-polarity solvents include but are not limited to chloroform, acetone, ethyl acetate, or a mixture of two or more of the preceding solvents. Preferably, column chromatography separation is conducted using methanol-treated DIAION column. For example, dip DIAION, which has the same weight as the dried *Plectranthus amboinicus* Benth, in methanol, and pack the methanol-treated DIAION into chromatography column. After pack, washing DIAION with methanol (one- to two-fold volume) then wash DIAION with double distilled water (five- to six-fold volume) and the packing is done.

Composition Analysis of the *Plectranthus amboinicus* Benth Extracts

Instruments and Equipment

High Performance Liquid Chromatography (HPLC)

Pump: Spectra-Physics P4000

Detector: UV/VIS Spectra-PhysicsSpectraSystem UV600OLP

Auto sampler: Thermo Separation Pruducts AS3500

Software: Thermo Separation Pruducts Chrom Quest

System Controller Thermo Separation Pruducts SN4000

1. Condition for Normal Phase HPLC

Chromatography column: Phenomenex, 4.6×250 nm, Luna 5u silica(2)

Flow rate: 1.0 ml/min Pressure Limit: 250 kgf/cm$^2$

Sample amount: 10 μl

PDA conditions: Sampling period: 0.64 sec

Wavelength range: 190-370 nm

Channels: 270, 320 nm

Elution Profile:

| | Time (min) | | | |
| --- | --- | --- | --- | --- |
| Mobile phase | 0 | 15 | 45 | 50 |
| n-hexane | 95% | 85% | 30% | 95% |
| Ethyl acetate | 5% | 15% | 70% | 5% |

2. Condition for Reverse Phase HPLC

Chromatography column: COSMOSIL, 4.6×250 nm, 5C15-MS

Flow rate: 1.0 ml/min Pressure Limit: 250 kgf/cm$^2$

Sample amount: 10 μl

PDA conditions: Sampling period: 0.64 sec

Wavelength range: 190-370 nm

Channels: 204, 254 nm

Elution Profile:

|  | Time (min) | | | |
| --- | --- | --- | --- | --- |
| Mobile phase | 0 | 10 | 55 | 60 |
| $H_2O$ | 90% | 90% | 20% | 80% |
| Acetonitrile | 10% | 10% | 80% | 20% |

According to the present invention, ointment containing *Plectranthus amboinicus* Benth extracts and *Centella asiatica* Urban extracts shows higher efficacy in enhancing healing of wounds than ointment containing *Plectranthus amboinicus* Benth crude extract and *Centella asiatica* Urban extract (shown in the example below). The optimum dosages of *Plectranthus amboinicus* Benth extracts and *Centella asiatica* Urban extracts in the ointment are about at least 0.01% and about at least 0.1% by weight respectively; preferably, *Plectranthus amboinicus* Benth extracts are about 0.01% to 5% by weight of the ointment and the *Centella asiatica* Urban extracts are about 0.1% to 20% by weight of the ointment, and the weight ratio between *Plectranthus amboinicus* Benth extracts and *Centella asiatica* extracts is about 1:60 to 1:4.

Persons skilled in the art should easily choose the suitable routes and the dosages for treatments. According to the present invention, the preferred route is topical administration. Dosage will depend on the nature and condition of the disorders, ages and health conditions of the patients, administration routes and any previous therapy. Persons skilled in the art should know that the dosage may vary depending on the individual's age, size, health condition and other related factors.

The invention is described in detail in the following examples. The following procedures are used to prove the effects of the composition comprising *Plectranthus amboinicus* Benth crude extracts or extracts and *Centella asiatica* Urban extracts in treating skin disorders, especially enhancing the healing of wounds for diabetic patients.

Example 1

*Plectranthus amboinicus* Benth Crude Extracts Obtained from Direct Extraction 1.25 g fresh *Plectranthus amboinicus* Benth was washed with water and juices were extracted with a juice extractor. The volume of the *Plectranthus amboinicus* Benth juices, measured by a graduated cylinder, is 1050 ml. The *Plectranthus amboinicus* Benth juices were freeze-dried and 19 g dry powders were obtained; the yield is 1.5%.

Example 2

Extracting *Plectranthus amboinicus* Benth Extracts (Named Hereinafter PA1, PA2 and PA3) Using Different Solvents 0.5 kg fresh *Plectranthus amboinicus* Benth was washed with water and juices were extracted with a juice extractor. 200 ml *Plectranthus amboinicus* Benth juices, measured by a graduated cylinder, were freeze-dried and 4.4 g dry powders were obtained; the yield is 0.9%.

4.4 g *Plectranthus amboinicus* Benth dry powders were added into 44 ml low-polarity solvents and extracted for 24 hours; the process was repeated twice. The two fluids extracted using the low polarity solvents were concentrated and dried, and 0.15 g PA3 was obtained; the yield is 3.4%.

The remaining *Plectranthus amboinicus* Benth dry powders, which were not extracted by the preceding step, were extracted again with 44 ml sub-high-polarity solvents for 24 hours; the process was repeated twice. The two fluids extracted using the sub-high-polarity solvents were concentrated and dried, and 1.19 g PA2 was obtained; the yield is 27%.

The remaining *Plectranthus amboinicus* Benth dry powders, which is not extracted by the proceeding step, were extracted again with 44 ml high polarity solvents for 24 hours, repeated twice. The two fluids extracted using the sub-high polarity solvents were concentrated and dried, and 1.83 g PA1 was obtained; the yield is 41.6%.

Example 3

*Plectranthus amboinicus* Benth Extracts (PAet, PA-F1, PA-F2, PA-F3 and PA-F4) Purified by Chromatography Column Separation 2 kg *Plectranthus amboinicus* Benth dry materials were dipped in ten-fold high-concentration alcohol for 24 hours. After filtration and a secondary dipping with ten-fold high-concentration alcohol for 24 hours, the *Plectranthus amboinicus* Benth extract fluids were concentrated by a reduced pressure rotary evaporator until the volume was 2-3% of the original volume (if dried, the powder is PAet, the weight is 30 g, the yield is 1.5%, and the chromatography spectrum is shown in FIG. 1).

The product obtained from the preceding step was diluted with solvent and loaded into a treated DIAION column. The column was eluted with double distilled water (ten-fold dry material volume) and a sample (labeled as PA-F1) was collected; the weight is 8.0 g and the yield is 0.4%.

Then, the column was eluted with medium-concentration alcohol (five- to ten-fold dry material volume) and a sample (labeled as PA-F2) was collected; the weight is 10.4 g and the yield is 0.52%.

The column was eluted again with high-concentration alcohol (five- to ten-fold dry material volume) and a sample (labeled as PA-F3) was collected; the weight is 16 g and the yield is 0.8%.

Figure 2:
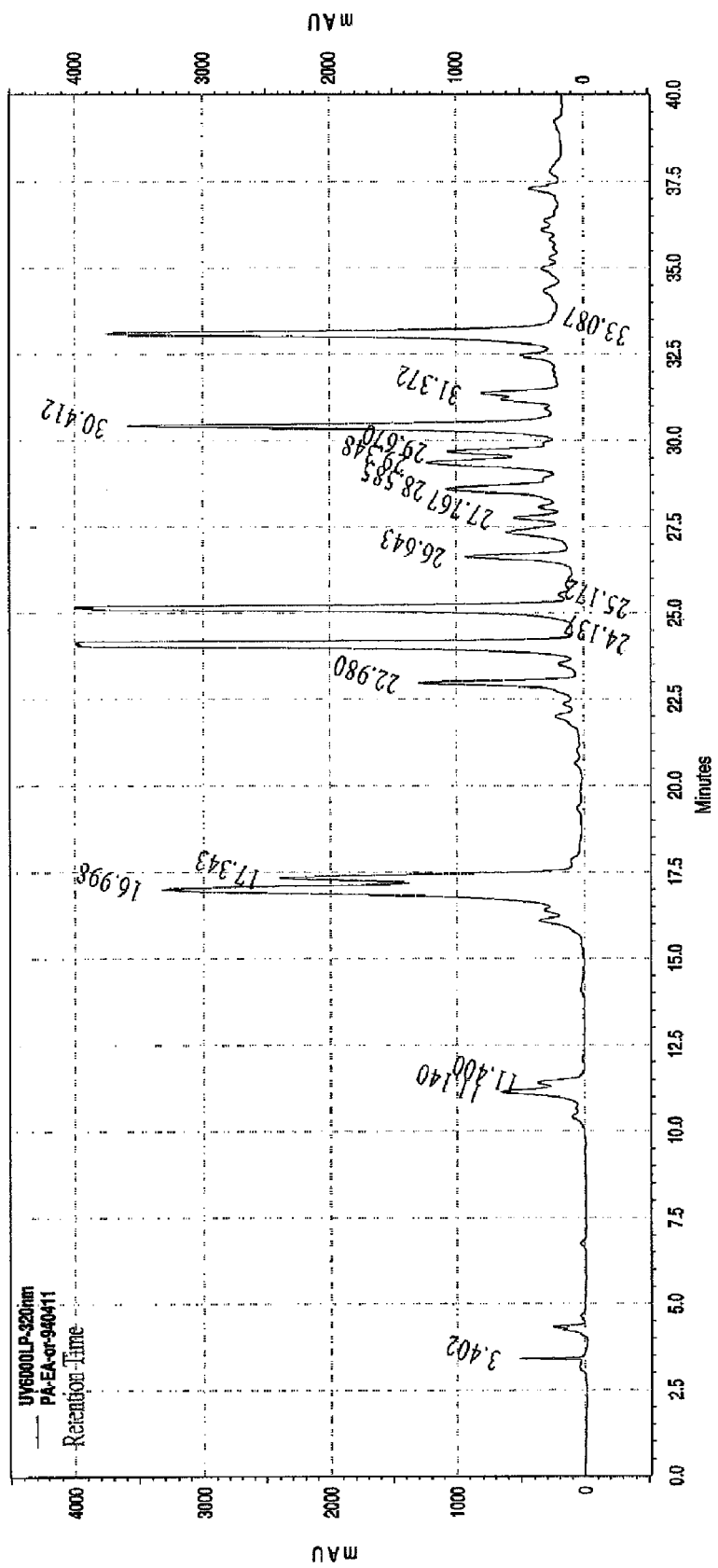
FIG. 2 shows the chromatography spectrum of column purified PA extracts (PA-F4) from alcohol-dipped, dried *Plectranthus amboinicus* Benth by Normal Phase HPLC at UV 320 nm.

Finally, the column was eluted with a solvent mixture of alcohol and ethyl acetate (five- to ten-fold dry material volume) and a sample (labeled as PA-F4) was collected; the weight is 13 g and the yield is 0.65%. The chromatography spectrum is shown in FIG. 2.

Example 4

Preparation for the Ointments Containing *Centella Asiatica* Urban Extracts and/or *Plectranthus amboinicus* Benth Extracts Using Ointment Base 1 g *Centella asiatica* Urban extract powders were added into 99 g ointment base, which was preheated in a water bath at about 50° C. until softened, to make the 1% *Centella asiatica* extract ointment.

The weight ratio of ointment base to *Plectranthus amboinicus* Benth extract was 99.75:0.25. The ointment base was preheated in a water bath at about 50° C. until softened and added in turn into the beaker containing frozen dried *Plectranthus amboinicus* Benth extracts to make the 0.25% *Plectranthus amboinicus* Benth extract ointment. 0.25% *Plectranthus amboinicus* Benth extract ointment was mixed with Centella asiatica Urban extracts in a weight ratio of 99:1 to make the 1% Centella asiatica extract+0.25% Plectranthus amboinicus Benth extract ointment.

Example 5

Animal Experiments for Wound Closures in Diabetic Rats

[Animal Experiments]
Induction of High Blood Sugar in the Animals
Rats were purchased and the high-blood-sugar induction with Streptozotocin (STZ) was conducted after their weights were over 300 g. The animals successfully induced to have high blood sugar (over 300 mg/DL) were selected to conduct the wound closure tests two months after showing high-blood-sugar syndromes.
Trauma Surgeries for the Diabetic Animals
i. The high-blood-sugar animals lower than 300 g in weight were eliminated and the rest were randomized into groups.
ii. The animals were anesthetized with pentobarbital and the hairs on the surgical area (dorsal area) were removed.
The surgical areas and instruments were then cleaned with alcohol before operation.
iii. The skins on the dorsal medium areas (4, 6 and 8 cm from the midpoint of two scapula) were excised (full thickness) using round cutting blades.
Measuring the Area of Wounds, Applying Medicaments, and Preventing the Wounds from Receiving Animal Scratches
i. A standard ruler was placed beside the wounds and pictures were taken.
ii. The wounds were given testing medicaments.
iii. The wounds were covered with gauze and hoods were worn on the rats' necks.
Medicaments were applied to the rats twice a day (in the morning and evening) and the wounds were measured at each time point.
After the experiments were finished, the regenerated skins were taken for biochemistry and histology analysis.
[Wound Area Analysis]
When taking pictures, a standard ruler was placed beside the wounds. Before analyzing the wounds with image pro, length was standardized with the standard ruler in the pictures to avoid the errors caused by different picturing distances.
[Data Analysis and Statistics]
The areas of the three wounds on the rats' backs were analyzed by image pro. The original wound areas were the areas of day zero. The original wound areas were substrated by the wound areas at different time points and then divided by the original wound areas to get the wound closure percentages. The mean of the three wound closure percentages of each rat represents the wound closure of each rat. 4 to 7 rats per group were used for each test. The data was shown as mean±standard error (SEM). The p-values of the testing results were calculated by t-test in statistics software sigma statis. P<0.05 means there is a significant difference, and it is marked with * on the statistics charts or tables. P<0.01 means there is a very significant difference, and it is marked with  on the statistics charts or tables. P<0.001 means there is an extremely significant difference, and it is marked with * on the statistics charts or tables.

Example 6

Figure 3:
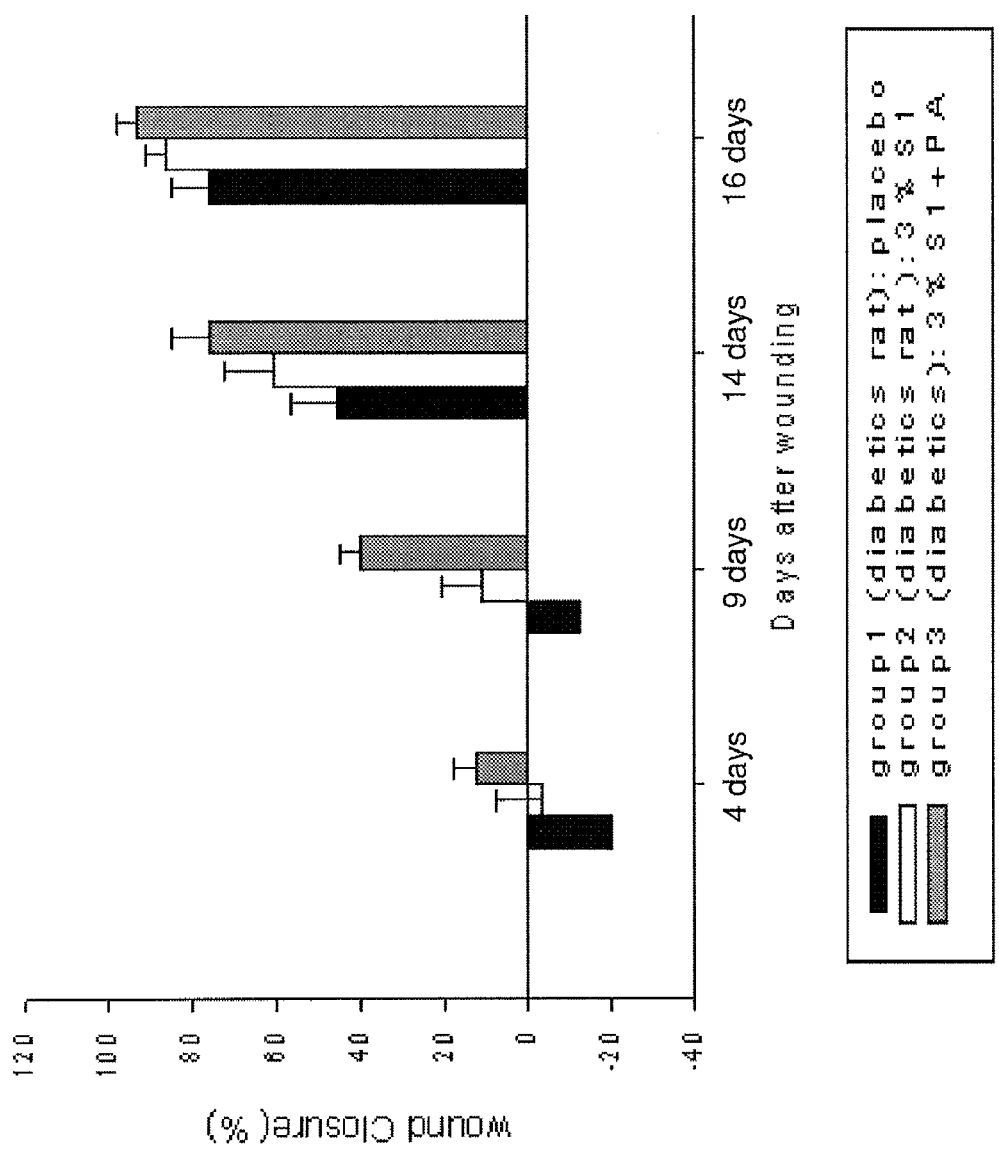
FIG. 3 shows wound closures in STZ-induced diabetic rats treated with *Centella asiatica* Urban extracts (S1) and *Plectranthus amboinicus* Benth (PA) crude extracts. Group 1: wound applied with ointment without medicament; group 2: wound applied with ointment containing 3% S1; group 3: wound applied with ointment containing 3% S1+2% PA crude extracts.

Effects of Centella asiatica Urban Extracts (S1) and Centella asiatica Urban Extracts+Plectranthus amboinicus Benth Crude Extracts (PA) on Wound Closures in STZ-Induced Diabetic Rats Plectranthus amboinicus Benth crude extracts and ointments were prepared according to the methods described in Examples 1 and 4 respectively. The wound closure animal experiments were conducted according to Example 5. The results are shown in FIG. 3 and Table 1.

TABLE 1

| Groups | Wound closure (%) | |
|---|---|---|
| | Day 4 | Day 9 |
| Group 1 Placebo | −19.92 ± 9.6 | −12.208 ± 7.0 |
| Group 2 3% S1 | −3.38 ± 11 | 11.12 ± 9.3 |
| Group 3 3% S1 + 2% PA | 12.8 ± 5.1 | 39.85 ± 4.8 |

The results show that the STZ induced rats treated with Plectranthus amboinicus Benth crude extracts and Centella asiatica Urban extracts have better wound closure effects than those treated with Centella asiatica Urban extracts alone.

Example 7

Figure 4:
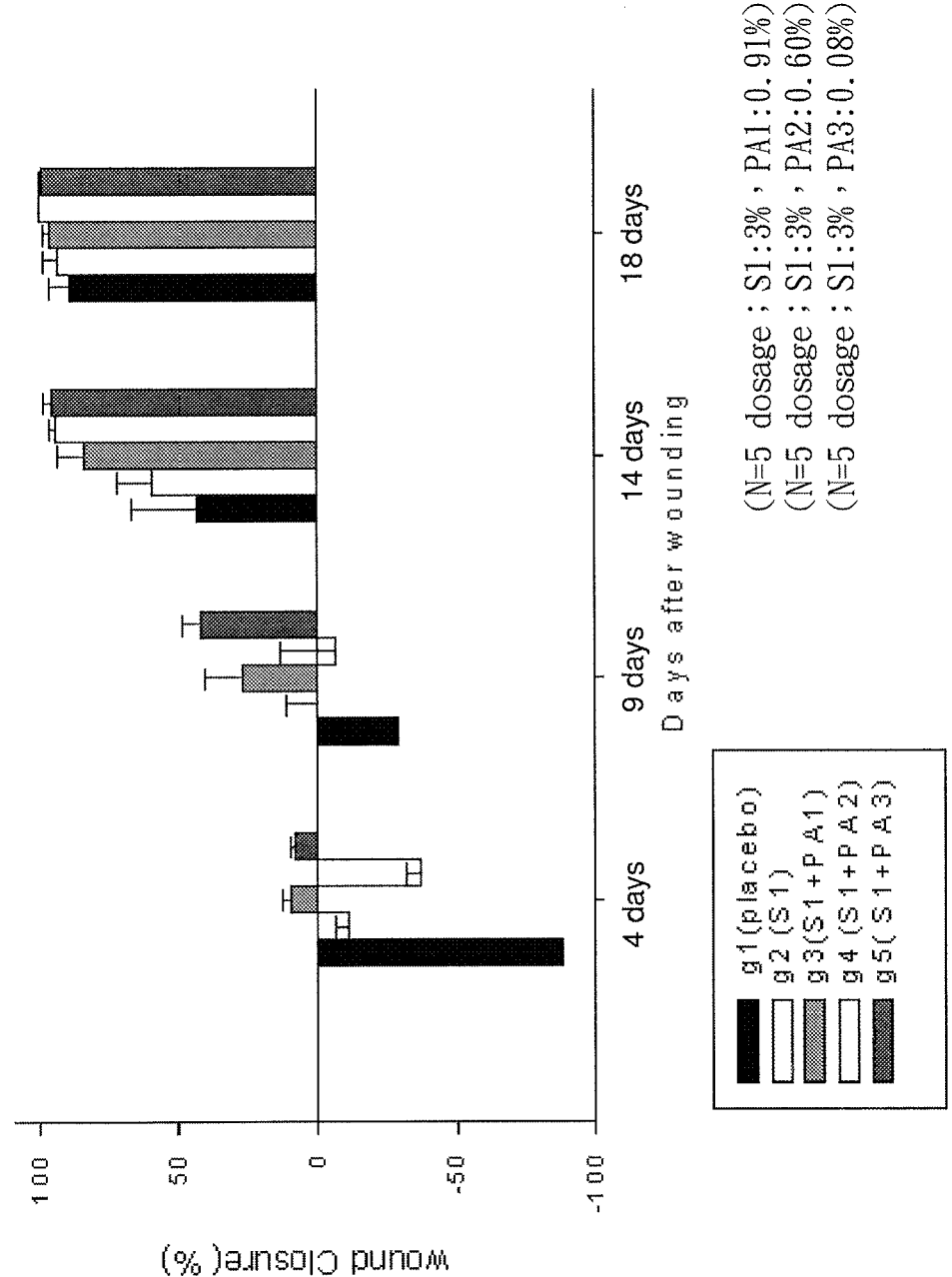
FIG. 4 shows wound closures in STZ-induced diabetic rats treated with S1 and PA extracts (PA1, PA2 and PA3) extracted with different solvents. Group 1: wound applied with ointment without medicament; group 2: wound applied with ointment containing 3% S1; group 3: wound applied with ointment containing 3% S1+PA1 extracts; group 4: wound applied with ointment containing 3% S1+PA2 extracts; group 5: wound applied with ointment containing 3% S1+PA3 extracts.

Effects of Centella asiatica Urban Extracts (S1) and Centella asiatica Urban Extracts+Plectranthus amboinicus Benth Extracts Extracted with Different Solvents (PA1, PA2 and PA3) on Wound Closures in STZ Induced Diabetic Rats Plectranthus amboinicus Benth extracts extracted with different solvents (PA1, PA2 and PA3) and ointments were prepared according to the methods described in Examples 2 and 4 respectively. The wound closure animal experiments were conducted according to Example 5. The results are shown in FIG. 4. Upon comparison of the five experiment groups, it is found that the wound closure percentages of group 3 and group 5 on day 4 and 9 are higher than those of group 1 and group 2. Group 2 is significantly better than group 1 (P<0.05). The effect of group 4 is not significant. In summary, the groups ranked by wound closure effects in STZ induced diabetic rats from high to low are groups 5 and 3, group 2, and group 1.

PA1, PA2 and PA3 were extracted from dry Plectranthus amboinicus Benth of the same weight. Due to the different yield (as shown in Example 2), PA3 has the lowest yield and its dosage is the lowest in this test. However, the ointment made of PA3 and Centella asiatica Urban extracts has the best effect on wound closure. *Centella asiatica* Urban extracts+*Plectranthus amboinicus* Benth extracts extracted with different solvents have a positive effect on wound closure.

Example 8

Effects of *Centella asiatica* Urban Extracts (S1) and *Centella asiatica* Urban Extracts+*Plectranthus amboinicus* Benth Extracts (PAet and PA-F3) on Wound Closures in STZ-Induced Diabetic Rats

Figure 5:
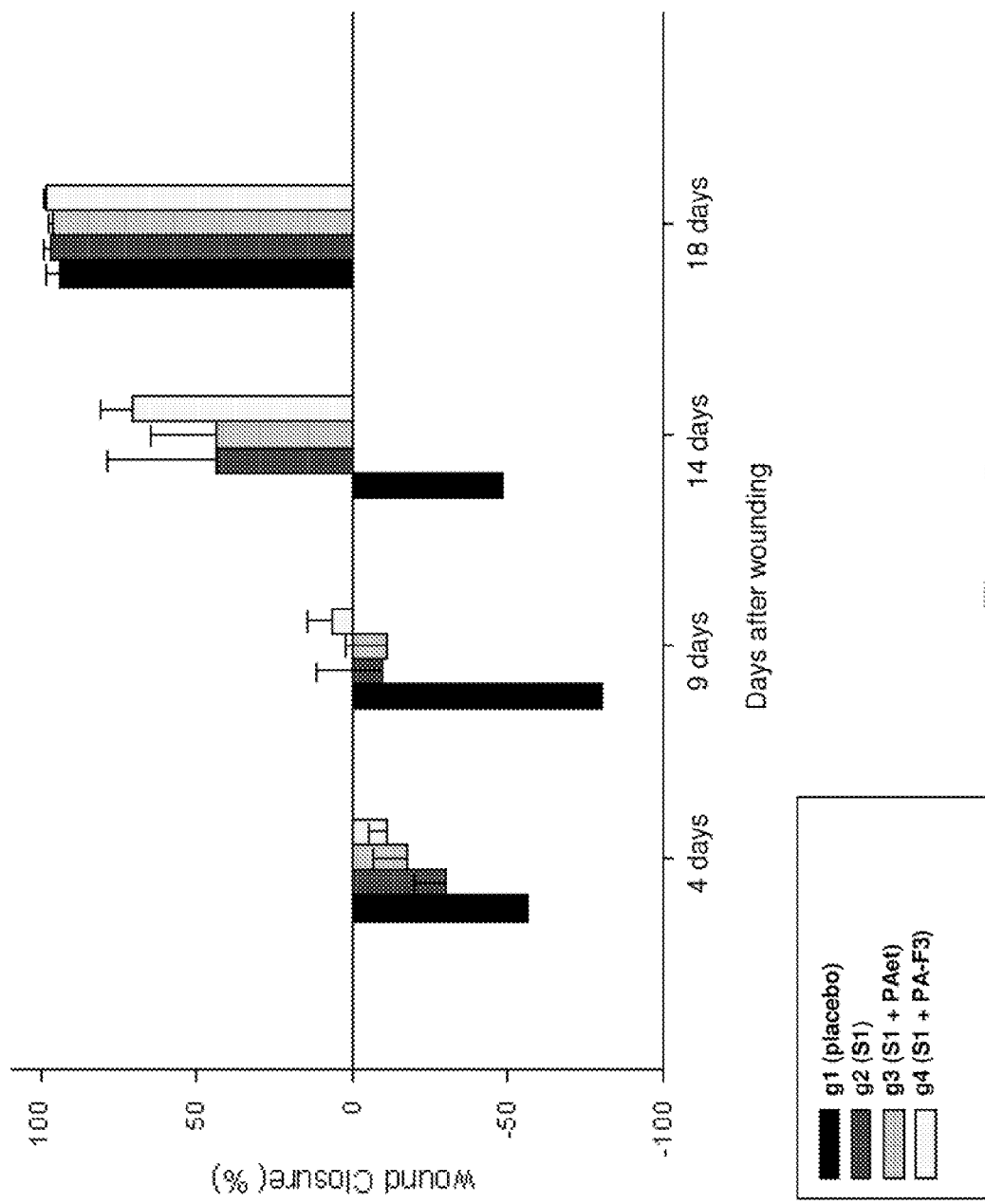
FIG. 5 shows wound closures in STZ-induced diabetic rats treated with S1, alcohol extracted PA extracts (PAet) and partially column purified PA extracts (PA-F3). Group 1: wound applied with ointment without medicament; group 2: wound applied with ointment containing 3% S1; group 3: wound applied with ointment containing 3% S1+PAet extracts; group 4: wound applied with ointment containing 3% S1+PA-F3 extracts.

*Plectranthus amboinicus* Benth extracts were prepared from alcohol extraction (PAet) and partial purification by column separation (PA-F3) according to methods described in Example 3. Ointments containing *Centella asiatica* Urban extracts+PAet and *Centella asiatica* Urban extracts+PA-F3 were prepared according to the methods described in Example 4. The wound closure animal experiments were conducted according to Example 5. The results are shown in FIG. 5. Upon comparison of group 1 (placebo), group 2 (3% *Centella asiatica* Urban extracts), group 3 (3% *Centella asiatica* Urban extracts+PAet) and group 4 (3% *Centella asiatica* Urban extracts+PA-F3), it is found that although the means show that group 1 is better than group 2 on day 4, 9 and 14, there is no significant difference. On day 4 and 9, group 3 is significantly better than group 4. In summary, the groups ranked by wound closure effects in STZ-induced diabetic rats from high to low are group 4, groups 3 and 2, and group 1.

Example 9

Effects of *Centella asiatica* Urban Extracts (S1) and *Centella asiatica* Urban Extracts+*Plectranthus amboinicus* Benth Extracts (PA-F1, PA-F2, PA-F3 and PA-F4) on Wound Closures in STZ-Induced Diabetic Rats

Figure 6:
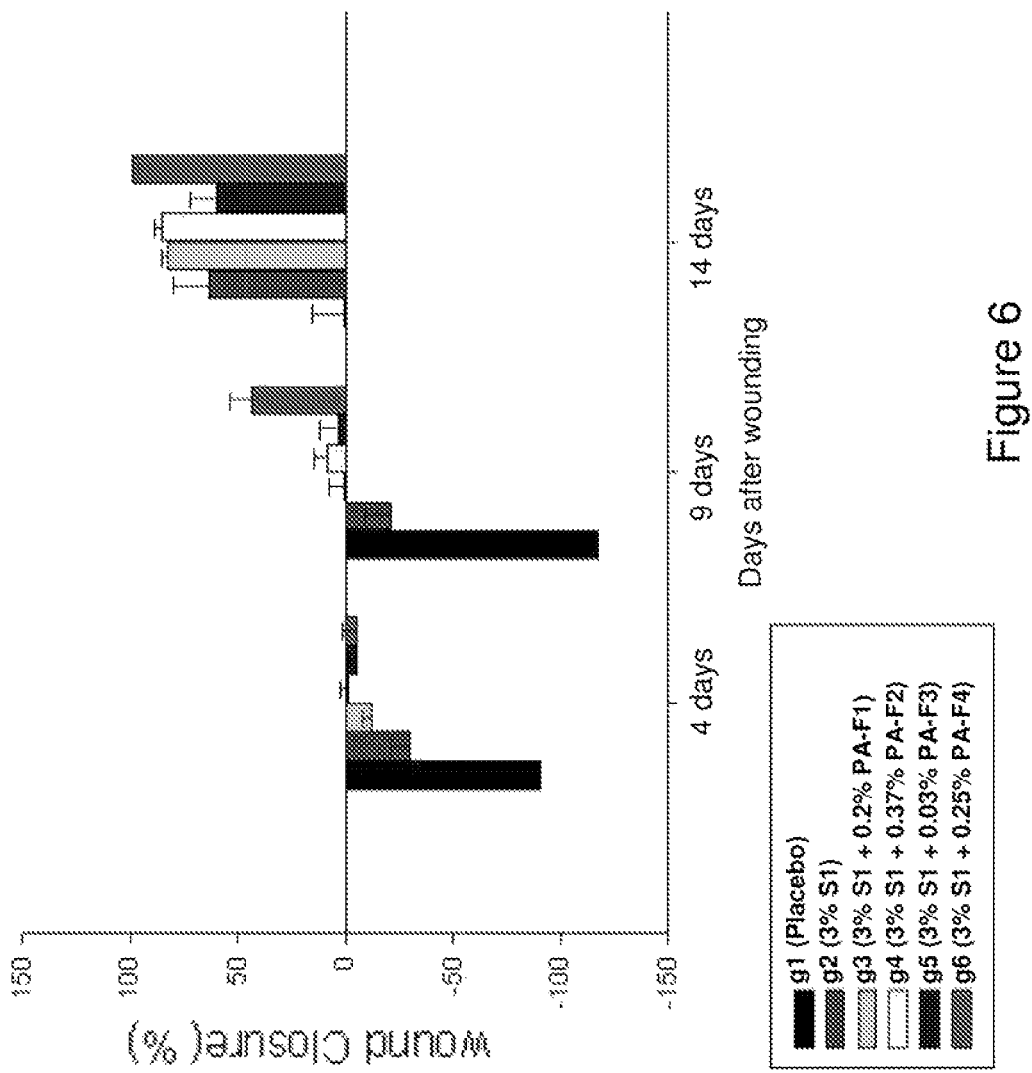
FIG. 6 shows wound closures in STZ-induced diabetic rats treated with S1 and column purified PA extracts (PAet, PA-F1, PA-F2, PA-F3 and PA-F4). Group 1: wound applied with ointment without medicament; group 2: wound applied with ointment containing 3% S1; group 3: wound applied with ointment containing 3% S1+0.2% PA-F1 extracts; group 4: wound applied with ointment containing 3% S1+0.37% PA-F2 extracts; group 5: wound applied with ointment containing 3% S1+0.03% PA-F3 extracts; group 6: wound applied with ointment containing 3% S1+0.25% PA-F4 extracts.

*Plectranthus amboinicus* Benth extracts (PA-F1, PA-F2, PA-F3 and PA-F4) were prepared from alcohol extraction and partial purification by column separation according to methods described in Example 3. Ointments containing *Plectranthus amboinicus* Benth extracts and *Centella asiatica* Urban extracts were prepared according to the methods described in Example 4. The wound closure animal experiments were conducted according to Example 5. The results are shown in FIG. 6 and Table 2.

3, group 2, and group 1. Especially, PA-F4+*Centella asiatica* Urban extracts have a very significant effect on wound closure in diabetic rats.

Example 10

Figure 7:
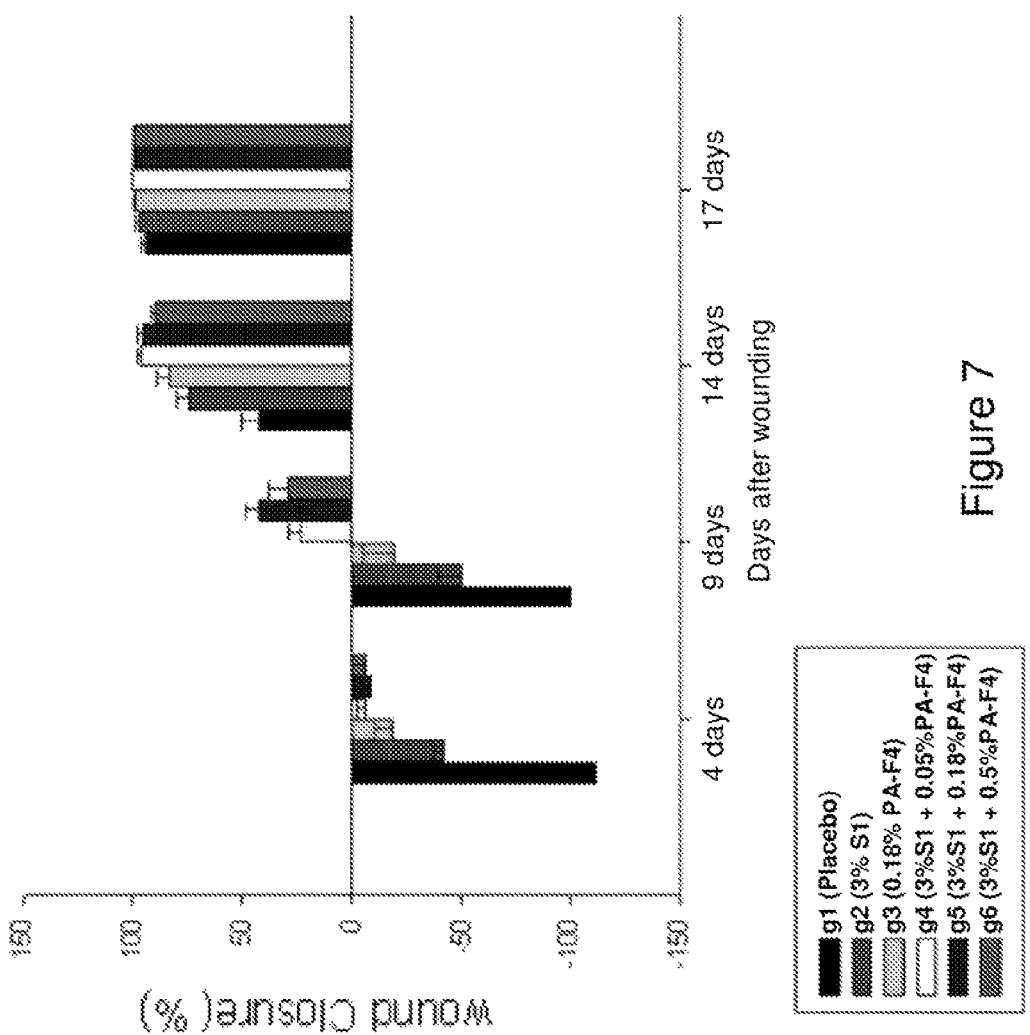
FIG. 7 shows wound closures in STZ-induced diabetic rats treated with S1 and PA-F4 extracts of different concentration. Group 1: wound applied with ointment without medicament; group 2: wound applied with ointment containing 3% S1; group 3: wound applied with ointment containing 0.18% PA-F4 extracts; group 4: wound applied with ointment containing 3% S1+0.05% PA-F4 extracts; group 5: wound applied with ointment containing 3% S1+0.18% PA-F4 extracts; group 6: wound applied with ointment containing 3% S1+0.5% PA-F4 extracts.

Effects of 3% *Centella asiatica* Urban Extracts (S1) and *Plectranthus amboinicus* Benth Extracts of Different Concentration on Wound Closures in STZ-Induced Diabetic Rats Ointments containing 3% *Centella asiatica* Urban extracts and *Plectranthus amboinicus* Benth extracts of different concentration were prepared according to methods described in Examples 3 and 4. The wound closure animal experiments were conducted according to Example 5. The results are shown in FIG. 7 and Table 3.

TABLE 3

| | | Wound closure (%) | | |
|---|---|---|---|---|
| Groups | | Day 4 | Day 9 | Day 14 |
| Group 1 | Placebo | −111.7 ± 10.3 | −100.3 ± 22 | 42.15 ± 8.6 |
| Group 2 | 3% S1 | −42.04 ± 4.4 | −50.23 ± 11.3 | 74.6 ± 5.3 |
| Group 3 | 0.18% PA-F4 | −18.80 ± 8.4 | −19.53 ± 14.6 | 83.78 ± 4.7 |
| Group 4 | 3% S1 + 0.05% PA-F4 | −6.08 ± 3.5 | −23.68 ± 5.3 | 96.12 ± 1.25 |
| Group 5 | 3% S1 + 0.18% PA-F4 | −8.5 ± 3.1 | 41.79 ± 6.3 | 95.1 ± 3.0 |
| Group 6 | 3% S1 + 0.5% PA-F4 | −6.5 ± 6.4 | 29.08 ± 8.5 | 89.5 ± 1.8 |

According to the data in Table 3, it is found that the wound closure percentages of groups 3, 4, 5 and 6 have significant to extremely significant differences compared to those of group 2 on day 4. On day 9, the wound closure percentages of groups 3, 4, 5 and 6 still have a significant difference compared to those of group 2. On day 14, only groups 4, 5 and 6 show significant to very significant differences in their wound closure percentages compared to group 2. Upon comparison of group 2 and group 3, it is found that the effect of group 3 is better than group 2 (having a significant difference on day 4); the combination effects are better. The results show that the effects on wound closures in diabetic rats of PA-F4 alone is better than that of *Centella asiatica* Urban extracts, and the

TABLE 2

| | | Wound closure (%) | | | | | |
|---|---|---|---|---|---|---|---|
| Groups | | Day 4 | Day 9 | | | | Day 14 |
| Group 1 | Placebo | −90.5 ± 11.1 | −117.8 ± 23.8 | | | | 0.47 ± 14.6 |
| Group 2 | 3% S1 | −29.8 ± 9.0 | −21.3 ± 12.6 | | | | 63.3 ± 16.4 |
| Group 3 | 3% S1 + 0.2% PA-F1 | −12.7 ± 4.9 | 0.49 ± 7.1 | | | | 82.5 ± 2.3 |
| Group 4 | 3% S1 + 0.37% PA-F2 | −1.3 ± 3.7 | 8.7 ± 6.2 | | | | 84.6 ± 3.4 |
| Group 5 | 3% S1 + 0.03% PA-F3 | −5.03 ± 3.8 | * | * | 3.3 ± 8.4 | ** ** | 59.7 ± 11.9 |
| Group 6 | 3% S1 + 0.25% PA-F4 | −5.7 ± 7.2 | | | 43.57 ± 10.4 | | 98.6 ± 0.7 |

On day 9, wound closure percentage of group 6 is significantly higher than groups 2, 3, 4 and 5. In summary, the groups ranked by wound closure effects in STZ-induced diabetic rats from high to low are group 6, group 4, groups 5 and combination of PA-F4 and *Centella asiatica* Urban extracts is much better than if they are used alone. The effective concentration of PA-F4 is 0.05% to 0.5%, and the preferred concentration is 0.18%.

Example 11

**Effects of 0.26% PA-F4 Extracts and *Centella asiatica* Urban Extracts (S1) of Different Concentration on Wound Closures in STZ-Induced Diabetic Rats**

Figure 8:
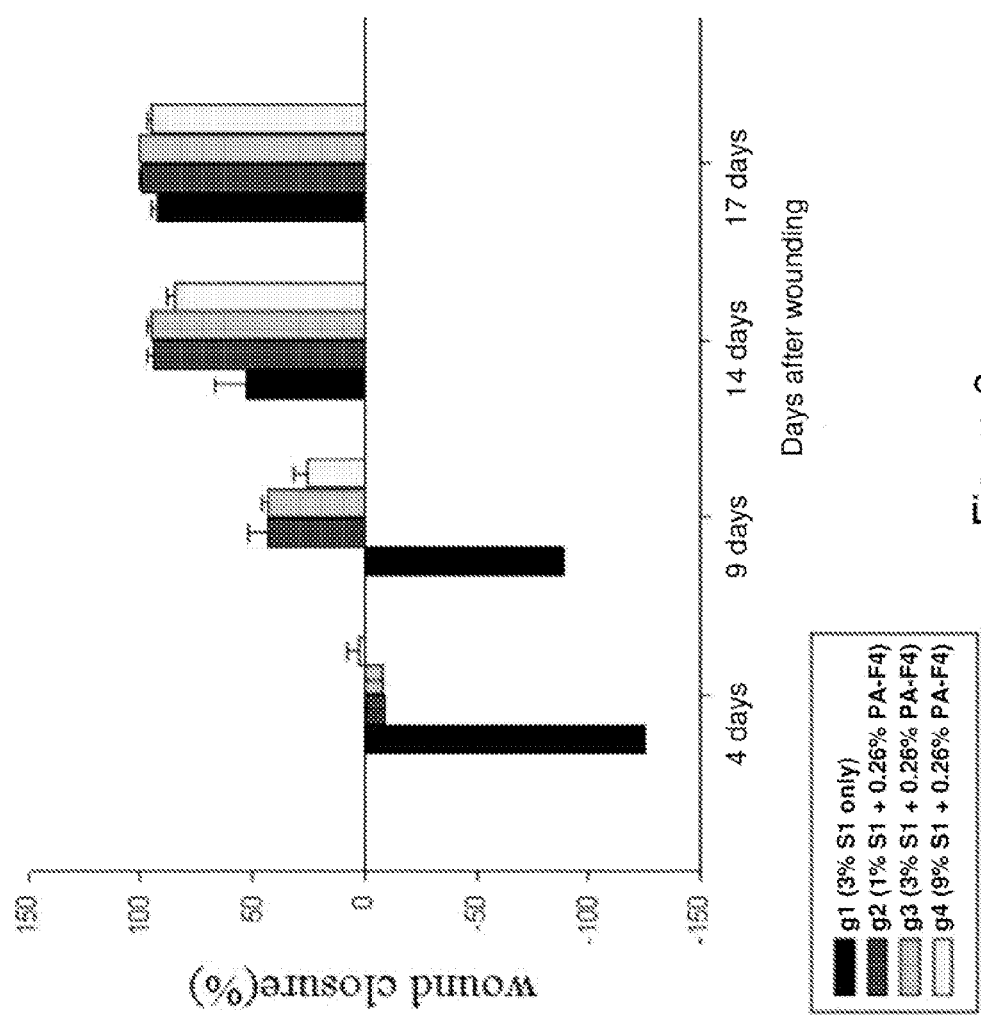
FIG. 8 shows wound closures in STZ-induced diabetic rats treated with PA-F4 extracts and S1 of different concentration. Group 1: wound applied with ointment containing 3% S1; group 4: wound applied with ointment containing 1% S1+0.26% PA-F4 extracts; group 5: wound applied with ointment containing 3% S1+0.26% PA-F4 extracts; group 6: wound applied with ointment containing 9% S1+0.26% PA-F4 extracts.

Ointments containing 0.26% PA-F4 and *Centella asiatica* Urban extracts of different concentration were prepared according to methods described in Examples 3 and 4. The wound closure animal experiments were conducted according to Example 5. The results are shown in FIG. 8 and Table 4. On day 4, the wound closure percentages of groups 4, 5 and 6 have extremely significant differences compared to those of group 1. On day 9, the wound closure percentages of groups 4, 5 and 6 have significant or very significant differences compared to those of group 1. On day 14, the wound closure percentages of groups 4 and 5 have significant or very significant differences compared to those of group 1. The results show that the effects on wound closures in diabetic rats using the combination of 0.26% PA-F4 and 1 to 9% of *Centella asiatica* Urban extracts is better than using *Centella asiatica* Urban extracts alone. The preferred concentration of *Centella asiatica* Urban extracts is 1 to 3%.

TABLE 4

| Groups | | Wound closure (%) | | |
| --- | --- | --- | --- | --- |
| | | Day 4 | Day 9 | Day 14 |
| Group 1 Placebo | | −125.1 ± 13 | −89.3 ± 26.1 | 56.3 ± 11 |
| Group 4 1% S1 + 0.26% PA-F4 | *** | −11.3 ± 7.3 | 42.8 ± 8.8 | 94.1 ± 2.6 |
| Group 5 3% S1 + 0.26% PA-F4 | | −8.0 ± 7.6 | 42.9 ± 2.7 | 95.0 ± 1.9 |
| Group 6 9% S1 + 0.26% PA-F4 | | 1.99 ± 5.9 | 25.8 ± 6.1 | 84.36 ± 3.8 |

Example 12

**Effects of PA-F4 and 3% *Centella asiatica* Urban Extracts (S1) on Wound Closures in db/db Mice**

Figure 9:
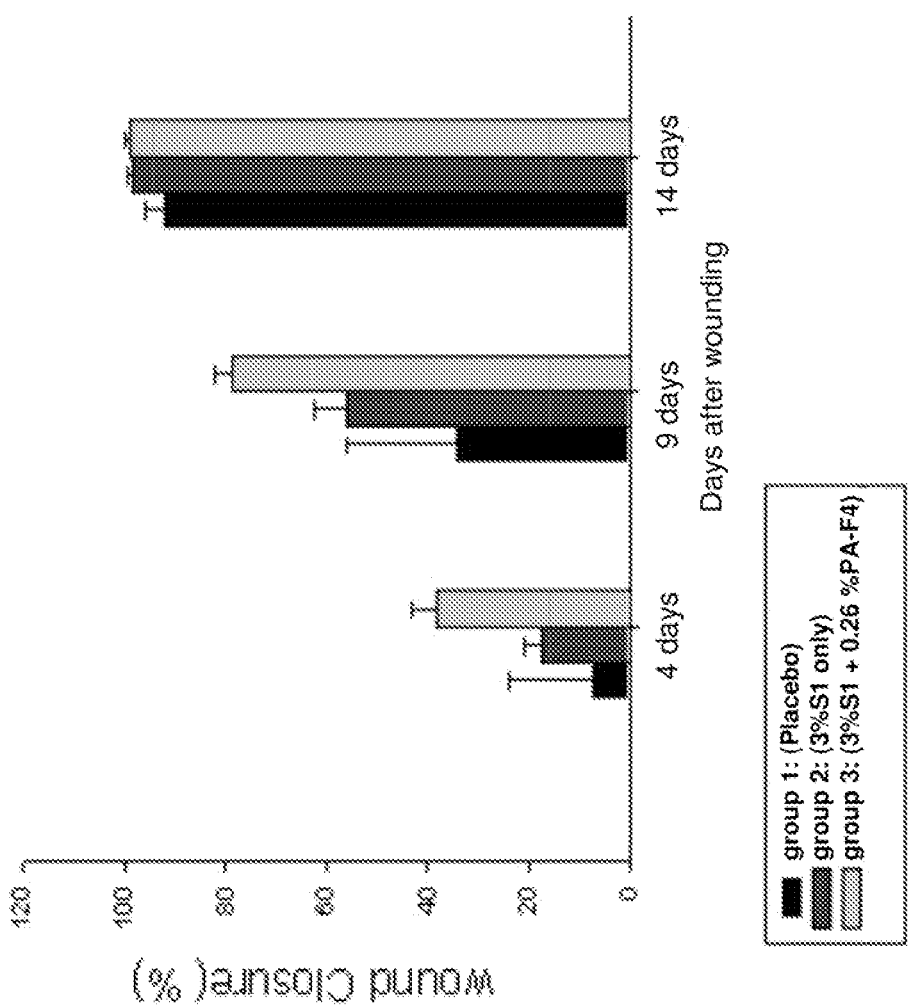
FIG. 9 shows wound closures in diabetic db/db mice treated with S1 and PA-F4 extracts. Group 1: wound applied with ointment without medicament; group 2: wound applied with ointment containing 3% S1; group 3: wound applied with ointment containing 3% S1+0.26% PA-F4 extracts.

Ointments containing 0.26% PA-F4 and *Centella asiatica* Urban extracts of different concentration were prepared according to methods described in Examples 3 and 4. The wound closure animal experiments were conducted according to Example 5. The results are shown in FIG. 9 and Table 5. Upon comparison of the three experiments, the degree of wound closure in group 3 (3% *Centella asiatica* Urban extracts+0.26% PA-F4) is significantly higher than group 2 (3% *Centella asiatica* Urban extracts), and very significantly higher than group 1 (placebo). The results show that 3% *Centella asiatica* Urban extracts+0.26% PA-F4 has a better effect on wound closure in diabetic db/db mice than 3% *Centella asiatica* Urban extracts alone, and is much better than a placebo without any medicament.

TABLE 5

| Groups | Wound closure (%) | |
| --- | --- | --- |
| | Day 4 | Day 9 |
| Group 1 Placebo | 7.04 ± 17.2 | 55.4 ± 5.0 |
| Group 2 3% S1 | 17.6 ± 3.4 | 56.1 ± 6.5 |
| Group 3 3% S1 + 0.26% PA-F4 | 38.4 ± 10.8 | 78.6 ± 7.3 |

What is claimed is:

1. A method for treating a skin disorder comprising administering a therapeutically effective amount of a composition comprising *Plectranthus amboinicus* Benth crude extracts or *Plectranthus amboinicus* Benth extracts and a therapeutically effective amount of *Centella asiatica* Urban extracts, wherein the *Plectranthus amboinicus* Benth crude extracts and *Plectranthus amboinicus* Benth extracts are obtained by a method comprising the steps of:

(a) extracting juices from whole *Plectranthus amboinicus* Benth plants directly with alcohol;

(b) concentrating the *Plectranthus amboinicus* Benth juices to obtain *Plectranthus amboinicus* Benth crude extracts;

(c) eluting the *Plectranthus amboinicus* Benth crude extracts with solvents by column separation; and (d) partially separating the solvent-eluted *Plectranthus amboinicus* Benth crude extracts to obtain *Plectranthus amboinicus* Benth extracts;

wherein the *Plectranthus amboinicus* Benth crude extracts have the following HPLC peak of retention time:

| Peak | Retention time (min) |
| --- | --- |
| 1 | 18.7 |
| 2 | 19.8 |
| 3 | 20.7 |
| 4 | 23.9 |
| 5 | 24.2 |
| 6 | 28.3 |
| 7 | 33.2 |
| 8 | 33.7 |
| 9 | 37.5 |
| 10 | 41.7 |
| 11 | 43.4 |
| 12 | 45.8 | wherein said HPLC is conducted at the condition of:
Flow rate: 1.0 ml/min Pressure Limit: 250 kgf/cm$^2$
Sample amount: 10 μl
PDA condition: Sampling period: 0.64 sec Wavelength range: 190-370 nm
Channel: 204, 254 nm
Elution Profile:

|  | Time (min) | | | |
| --- | --- | --- | --- | --- |
| Mobile phase | 0 | 10 | 55 | 60 |
| $H_2O$ | 90% | 90% | 20% | 80% |
| Acetonitrile | 10% | 10% | 80% | 20% | and wherein the *Plectranthus amboinicus* Benth extracts have the following HPLC peak of retention time:

| Peak | Retention time (min) |
| --- | --- |
| 1 | 11.1 |
| 2 | 11.4 |
| 3 | 16.9 |
| 4 | 17.3 |
| 5 | 22.9 |
| 6 | 24.1 |
| 7 | 25.1 |
| 8 | 26.6 |
| 9 | 27.7 |
| 10 | 28.5 |
| 11 | 29.3 |
| 12 | 29.6 |
| 13 | 30.4 |
| 14 | 31.3 |
| 15 | 33.0 | wherein said HPLC is conducted at the condition of:
Flow rate: 1.0 ml/min Pressure Limit: 250 kgf/cm$^2$
Sample amount: 10 μl
PDA conditions: Sampling period: 0.64 sec
Wavelength range: 190-370 nm
Channels: 270, 320 nm
Elution Profile:

|  | Time (min) | | | |
| --- | --- | --- | --- | --- |
| Mobile phase | 0 | 15 | 45 | 50 |
| n-hexane | 95% | 85% | 30% | 95% |
| Ethyl acetate | 5% | 15% | 70% | 5% |

2. The method according to claim 1, wherein said skin disorder is general trauma or bedsores.

3. The method according to claim 1, wherein the skin disorder is a wound in a diabetic patient.

* * * * *